United States Patent [19]

Plotkin et al.

[11] Patent Number: 5,276,174

[45] Date of Patent: Jan. 4, 1994

[54] ALK-1-ENYLOXY CARBONATES

[75] Inventors: Jeffrey S. Plotkin, Monsey, N.Y.; Kolazi S. Narayanan, Palisades Park; Paul D. Taylor, West Milford, both of N.J.

[73] Assignee: ISP Investments Inc., Wilmington, Del.

[21] Appl. No.: 491,362

[22] Filed: Mar. 9, 1990

[51] Int. Cl.$^5$ .............................................. C07C 69/96
[52] U.S. Cl. .................................. 558/266; 558/265; 558/268; 558/275; 558/276
[58] Field of Search ............... 558/266, 265, 268, 275, 558/276

[56] References Cited

U.S. PATENT DOCUMENTS

| | | | |
|---|---|---|---|
| 2,384,125 | 9/1945 | Muskat et al. | 558/266 X |
| 2,384,143 | 9/1945 | Strain et al. | 558/265 x |
| 2,385,933 | 10/1945 | Muskat et al. | 558/266 X |
| 4,156,035 | 5/1979 | Tsao | 427/44 |
| 4,273,726 | 6/1981 | Altuglu | 558/266 X |
| 4,293,503 | 10/1981 | Young | 558/266 X |
| 4,654,379 | 3/1987 | Lapin | 522/15 |

OTHER PUBLICATIONS

J. A. Dougherty and F. J. Vara, L. R. Anderson, "Radcure '86": Conference Proceedings, Association for Finishing Process, Baltimore, 1986, 15–1.

J. A. Dougherty and F. J. Vara, "Radcure Europe '87": Conference Proceedings, Association for Finishing Processes, Munich, West Germany, 1987, 5–1.

J. V. Crivello, J. L. Lee, D. A. Conlon, "Radiation Curing VI: Conference Proceedings", Association for Finishing Processes, Chicago, 1982, 4–28.

S. C. Lapin, "Radcure '86: Conference Proceedings", Association for Finishing Processes, Baltimore, 1986, 15–15.

S. C. Lapin, "RadTech '88—North America: Conference Proceedings" RadTech International, New Orleans, 1988, p. 395.

A. D. Ketley and Jung-Hsien Tsao, J. Radiation Curing., Apr., 1979, p. 22.

W. C. Perkins, J. Radiation Curing, Jan., 1981; p. 16.

P. C. Nelson and E. J. Moran, "RadTech '88—North America: Conference Proceedings", RadTech International, New Orleans, 1988; p. 120.

B. L. Braunn, "RadTech Europe '89: Conference Proceedings", Radtech Europe, Florence, 1989, p. 565.

F. J. Vara and Jim Dougherty, Radcure '89 Conference Proceedings, "Concurrent Cationic/Free Radical Polymerization of Vinyl Ethers with Acrylate Functional Oligomers".

F. J. Vara and J. A. Dougherty, Water-Borne and Higher-Solids Coating Symposium, Feb. 1990, "Vinyl Ether in UV and EB Induced Cationic Curing".

Primary Examiner—Joseé G. Dees
Assistant Examiner—Joseph M. Conrad
Attorney, Agent, or Firm—Marilyn J. Maue; Joshua J. Ward

[57] ABSTRACT

This invention relates to radiation curable alk-1-enyloxy carbonate reaction products of a polyhydroxylated compound having the formula ROH and a dialk-1-enyloxy carbonate having the formula

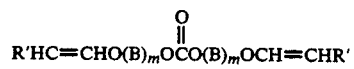

wherein R is a $C_3$ to $C_{50}$ saturated or unsaturated, linear, branched or cyclic polyhydroxylated hydrocarbon radical optionally substituted with halo, alkoxy, lower alkyl, cyano or nitro;

R' is hydrogen or lower alkyl

B is a linear, branched or cyclic divalent radical having from 2 to 12 carbon atoms and is selected from the group of alkylene, mono- or poly- alkoxylated alkylene, alkenylene, alkynylene, arylene, alkarylene and aralkylene radicals, which radicals are optionally substituted with halo, lower alkyl, cyano, nitro or alkoxy and m has a value of from 1 to 10. The products of this invention are defined by the formula:

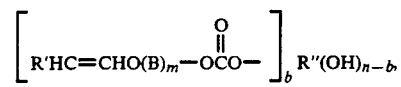

wherein R" is the same as R except that it contains at least one less hydroxy group; (b) has a value of at least 1 up to the number of hydroxy groups in ROH and (n) represents the number of hydroxy groups in ROH.

6 Claims, No Drawings

ALK-1-ENYLOXY CARBONATES

In one aspect the invention relates to alk-1-enyloxy carbonates which are rapidly curable by cationically initiated radiation. In another aspect the invention relates to the use of said products as protective coatings or as photoresist materials.

BACKGROUND OF THE INVENTION

Free radical induced radiation curable coatings and films are normally formulated with acrylate monomer diluents and acrylate functional oligomers. The formulations usually contain minor amounts of additive ingredients such as surfactants, slip agents, defoamers, thickeners, and/or thixothopes. Representative oligomers are the acrylate functional end capped urethane polyesters, polyols and acrylate functional end capped bisphenol A epoxy and novalic epoxy resins.

Since acrylates are not conducive to cationically induced radiation curing, they require free radical systems which are oxygen inhibited unless reacted in an inert atmosphere, generally under a blanket of nitrogen. Although formulation with a photoinitiator which undergoes bimolecular reaction with a hydrogen donor minimizes the inhibitory effect of air, this benefit is realized at the expense of a greatly reduced cure rate. Also, it is found that polymerization or curing in free radical systems ceases almost immediately upon removal from the source of radiation; thus, the cured product often contains some unpolymerized components. Accordingly, it is an aim of research to develop an oligomer having the beneficial properties of acrylates but which is amenable to radiation curing at a rapid rate by cationically induced polymerization which is not oxygen inhibited and which permits continued polymerization after removal from the source of radiation exposure.

It has also been found that acrylate formulations when stored under normal condition require the addition of a free radical scavenger such as substituted hydroquinones and phenothiazine to achieve long term stability. However, after the stored coating is applied on a substrate, the inhibitory effect of the stabilizer significantly reduces the cure rate.

Finally, it is noted that the unsubstituted acrylates are sensitizers and skin irritants as well as being carcinogenic, so that specialized safety precautions must be taken to protect operators from exposure. Although alkoxylation has lessened irritancy of the acrylates, their carcinogenic properties are not reduced.

Accordingly it is an object of the present invention to overcome the above described deficiencies by employing an economical and commercially acceptable compound or composition and curing process.

Another object of this invention is to utilize a multifunctional cross-linking agent, which is itself a polymerizable viscous liquid and which assists rapid radiation curing when formulated with allyl, epoxide or acrylate monomers and oligomers.

Another object is to provide a non-toxic cross linkable compound which is suitably cured as a film or as a coating on a substrate and which possesses good adhesion, high abrasion resistance and resistance to chemical attack in both acid or basic media.

Still another object is to provide a more economical process for cross-linking monomeric or polymeric acrylates or epoxides within a few seconds which can be effected in the presence of air.

Another object is to provide a compound which is curable at a rapid rate by cationically induced radiation.

Yet another object is to provide a substrate coated with a rigid scratch resistant and chemical resistant coating.

These and other objects will become apparent from the following description and disclosure.

THE INVENTION

In accordance with this invention there is provided a polymerizable compound having the formula

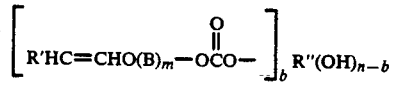

which is the reaction product of a polyhydroxylated reactant (I) having the formula ROH and a dialkenyloxy carbonate coreactant (II) having the formula:

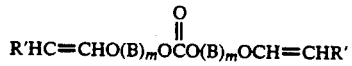

wherein
R is a $C_3$ to $C_{50}$ saturated or unsaturated, linear, branched or cyclic polyhydroxylated hydrocarbon radical optionally substituted with halo, alkoxy, lower alkyl, cyano or nitro;
R' is hydrogen or lower alkyl
R" is the same as R except that it contains at least one less hydroxy group.
B is a linear, branched or cyclic divalent radical having from 2 to 12 carbon atoms and is selected from the group of alkylene, mono- or poly- alkoxylated alkylene, alkenylene, alkynylene, arylene, alkarylene and aralkylene radicals, which radicals are optionally substituted with halo, lower alkyl, cyano, nitro or alkoxy (m) has a value of from 1 to 10; (b) has a value of from at least 1 up to the number of hydroxy groups in ROH and (n) represents the number of hydroxy groups in ROH, generally from 3 to 10 hydroxy groups.

Polyhydroxylated reactant (I) contains at least 3, preferably not more than 10, hydroxy groups and includes hydroxylated derivatives of alkylene, alkenylene, alkynylene, arylene, alkarylene, aralkylene and ethoxylated or propoxylated species of these radicals. Specific examples of hydroxylated reactant (I) are represented by trihydroxy benzene, trihydroxy nitrobenzene, tetrahydroxy diphenyl dimethyl methane, hexahydroxy diphenyl methane, tetrahydroxy styrene, tetrahydroxy toluene, dichlorotrihydroxy benzene, trihydroxy cyanomethyl benzene, dinitrotrihydroxybenzene, hexahydroxy anthranol, and alkoxylated derivatives thereof 1,2,5,7,9-pentahydroxynonane, 1,2,4-trihydroxybutane, 4,5-dichloro-1,3,6,10-tetrahydroxydecane, decahydroxy tetracosane, decahydroxy pentacontane, 1,2,11,12-tetrahydroxy dodec-6-yne, 3,5-bromo-1,2,13,14-tetradecane, trimethylol ethane, trimethylol propane, 3-ethoxy-1,2,4,5-tetrahydroxypentane, pentaerythritol, starches, cellulose, sugars and alkoxylated drivatives thereof.

The dialkenyloxy carbonate coreactants (II) are those compounds described in copending application FDN-1757 and are preferably those wherein R' is hydrogen or methyl, m is 1 and B is butylene, dimethylene cyclohexane or ethoxylated or propoxylated derivatives thereof. Examples of suitable coreactants include bis(ethenyloxy butyl) carbonate, bis(ethenyloxy dimethylcyclohexyl) carbonate, bis(prop-1-enyloxy butyl) carbonate, and the polyethoxylated or polypropoxylated derivatives thereof, such as for example the polyethoxylated derivative of bis(ethenyloxy butyl) carbonate, having the formula

wherein p has a value of from 1 to 10.

The products of the present reaction comprise individual compounds or mixtures of compounds within the scope of the above formula. Also included, are mixtures of one or more compounds having the above formula. Such mixtures or individual compounds are suitable for crosslinking with other monomers or oligomers by cationically induced radiation at a high cure rate. The individual compounds or mixtures of the present products are also homopolymerizable to a highly branched dense structure which provides superior scratch resistance and resistant to attack by acids, bases and solvents. The density of the cured structure is in part dependent upon the number of substituted hydroxy groups in reactant (I); however, even products containing only 3 alkenyloxy alkyl carbonate groups exhibit these properties. The products having one or two alkenyloxy alkyl carbonate groups and at least one hydroxy group provide a more flexible coating, which for certain applications is desirable.

The reaction for synthesizing the above compounds is conducted in the presence of between about 0.01 and about 5 wt. %, preferably between about 0.1 and about 1 wt. % of a basic catalyst such as particulate sodium, potassium or lithium metal, sodium, potassium or lithium hydroxide, hydride or alkoxide, e.g. methoxide, and the like. The reactants may be diluted with up to 80% of a suitable inert solvent such as xylene, toluene, tetrahydrofuran, N-methylpyrrolidone, dimethylformamide, etc. Although dilution is usually recommended for more viscous reaction mixtures, it is also within the scope of this invention to carry out the reaction in the absence of solvent.

The reaction conditions include a temperature of from about 50° to about 200° C., a pressure of from about 1 mm Hg to about 100 atmospheres for a period of from about 0.5 to about 24 hours. Within the above operating parameters, between about 90° and about 120° C. under from about 1 to about 10 mm Hg for a period of from about 3 to about 7 hours are preferred. High conversions in excess of 80% are achieved by the present reaction.

The ratio of polyhydroxylated reactant to dialkenyloxy alkyl carbonate is as close to stoichiometry of the product desired as is convenient to maintain. Desirably, the amount of dialkenyloxy alkyl carbonate varies from about 1 to about 2 moles of carbonate per equivalent of hydroxyl groups. However, it is to be understood that excess amounts of the alkenyloxy alkyl carbonate, up to about a 10 mole excess, can be employed without detriment to the reaction; the only objection being that such high excesses of the carbonate reactant are wasteful and inefficient.

The crude product of the above reaction generally contains a mixture of products. Thus for example when ROH is HOCH$_2$—CH(OH)CH(OH)CH$_2$OH the crude product contains one or more of the following derivatives, depending upon the amount of coreactant employed.

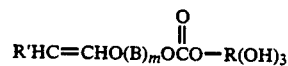

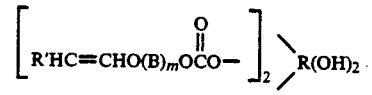

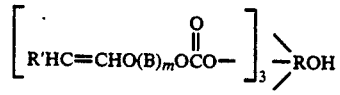

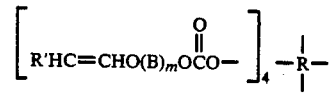

The products can be separated by any conventional means, e.g. fractional distillation, if desired.

The above compounds or mixtures, either alone or formulated in admixture with other copolymerizable monomers or oligomers in amounts up to about 50%, can be applied to a substrate in a thickness of from about 0.1 to about 20 mils, preferably from about 0.5 to about 10 mils. Suitable substrates include glass, ceramic, metal, plastic, wood, masonary and fabrics. The coated material is then subjected to curing from a source of radiation.

Curing is effected in the presence of a cationic photoinitiator such as an onium salt, for example the triphenyl sulfonium salt of phosphorous hexafluoride, diphenyl iodium salt, tetrazolium chloride, phenyl onium salts or aryl alkyl onium salts and the like or any of the photoinitiators described by James A. Crivello et al., (RADIATION CURING IV CONFERENCE PROCEEDINGS 1982, pages 4-28 to 4-39, Chicago) in the article entitled "New Monomers for Cationic UV-Curing". The amount of initiator employed is generally between about 0.05 and about 5 wt. %, preferably between about 0.1 and about 2 wt. % with respect to reactants. The initiators suitable to effect polymerization reactions of the present invention can also comprise a mixture including the above named cationic initiators and a free radical initiator to provide a hybrid initiated system. Suitable free radical initiators include 1-hydrocyclohexyl phenyl ketone (e.g. IRGACURE 184), 2-hydroxy-2-methyl-1-phenyl-1-propan-1-one (DAROCUR 1173), 2,2-dichloro-1-(4-phenoxyphenyl) ethanone (SANDORAY 1000) and the like and other free radical and cationic initiators which are described by M. J. M. Abadie, Advantages and Development of Photochemical Initiators, in the European Coatings Journal 5/1988, pages 350-358. When initiator mixtures are employed, the free radical component can comprise up to 75%, preferably between about 30 and about 70%, of the initiator component. A particularly preferred initiator mixture includes between about 30 wt. % and about 40 wt. % of FX-512 (60% aromatic complex sulfonium salt in 40% butyrolactone) and between about 60 and about 70% of IRGACURE 184. The present cationic initiator or cationic free radical mixtures are recommended for cross linking blends of the present vinyl ether carbonate and a polymerizable vinyl ether or epoxide comonomer. When the blend includes an acrylate, initiator mixtures are recommended. The curing is accomplished within a few seconds, most often within a period of less than one second, by exposure to a source of radiation such as UV light exposure at 100 to 1500, preferably at 200 to 600, millijoules/cm$^2$. Equivalent dosages for curing are employed when using alternative radiation sources, such as lazer emission or electron beam exposures. For example, curing with an electron beam is carried out at between about 0.5 and about 20, preferably between about 1 and about 10, megarads. Specific techniques for radiation curing are well known, thus further amplification is not required.

As inferred above, the present products can be mixed with a vinyl ether, epoxide, acrylate or vinyloxy alkyl urethane monomer or polymer to incorporate and combine the advantages of instant compounds with the beneficial properties of those coating materials which otherwise would not be amenable to cationic radiation curing. Specific examples of monomers or polymers with which the present products can be combined to form coatings include vinyl cyclohexane epoxide, alkyl methacrylates and acrylates, vinyloxy butyl urethane, 1,4-butanediol diglycidyl ether, 3,4-epoxycyclohexyl methyl-3,4-epoxy cyclohexane carboxylate; the diglycidyl ethers of bisphenol A or bisphenol F; polyglycidyl ethers of phenol-formaldehyde, e.g. epoxy novolac resins and compounds disclosed in the HANDBOOK OF EPOXY RESINS by Henry Lee and K. Neville, published by McGraw Hill, 1967, and other functional monomers and polymers which possess properties beneficial in durable protective coatings. When such comonomeric coatings are employed, the mixture contains at least 25% of the present carbonate or mixtures of carbonates or oligomers thereof.

These mixtures can also contain a silicone or fluorocarbon surfactant, e.g. FC-430, a fluoroaliphatic polymeric ester supplied by Minnesota Mining and Manufacturing Company.

The homopolymerized and copolymerized products of this invention have an extremely high cross-linked density and thus display superior resistance to solvents, acids and bases and form hard abrasion resistant films and coatings, possessing good substrate substantivity. The individual products of this invention, as monomers or oligomers or as mixtures thereof are also useful as chemical intermediates and as materials which, upon hydrolysis, are capable of forming hydrogels. Also, because of their high radiation sensitivity, the present compounds are suitable as photoresist materials.

Having thus described the invention reference is now had to the accompanying examples which illustrate preferred embodiments but which are not to be construed and limiting to the scope of the invention as more broadly defined above and in the appended claims.

EXAMPLE 1

In a 250 ml round bottom flask 25 g. of 3,3,3-trimethylolpropane was charged along with 143 g. of bis(ethenyloxybutyl) carbonate and 0.1 g. of sodium methoxide. The contents of the flask was heated to 100°–105° C. under a vacuum of 3 mm Hg. After 6 hours, 54 g. of hydroxybutyl vinyl ether had been distilled out of the reaction flask. After cooling, the crude reaction product was treated with 2 g. of charcoal at 45° C. and filtered, leaving a yellowish viscous liquid. The $_1$H NMR and IR spectrum of this material indicated the mixture of products shown

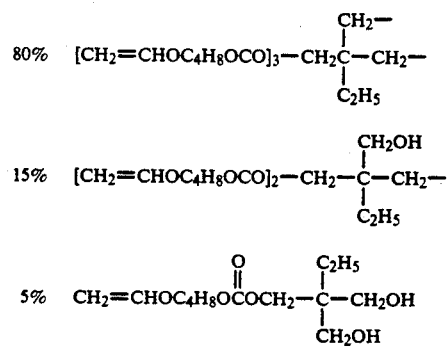

EXAMPLE 2

The product from Example 1 is mixed with an equal weight of triethylene glycol divinyl ether, 1 phr (part per hundred) fluorochemical surfactant (FC-430) and 4 phr cationic photoinitiator (FX-512). The resulting low viscosity liquid is coated on a polyester substrate (2.0 mil thickness) and exposed to 400 millijoules/cm$^2$ from a mercury vapor lamp. A tack free, chemically resistant coating is produced.

EXAMPLE 3

Example 1 was repeated except that 25 g. of 1,2,6-trihydroxyhexane was substituted for trimethylolpropane. The resulting product was a yellow viscous oil. The $^1$H NMR and IR spectra of this material indicated a mixture of the compounds:

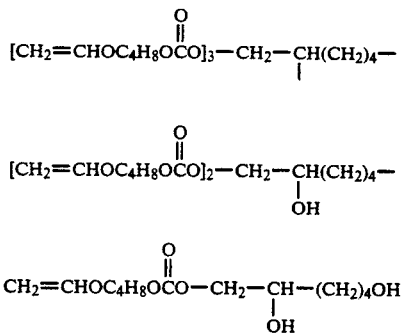

and isomers thereof.

What is claimed is:

1. A compound having the formula

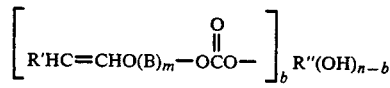

wherein

R'' is a C$_3$ to C$_{50}$ saturated or unsaturated, linear, branched or cyclic hydrocarbon radical optionally substituted with halo, alkoxy, lower alkyl, cyano or nitro;

R' is hydrogen or lower alkyl

B is a linear, branched or cyclic divalent radical having from 2 to 12 carbon atoms and is selected from the group of alkylene, mono- or poly- alkoxylated alkylene, alkenylene, alkynylene, arylene, alkarylene and aralkylene radicals, which radicals are optionally substituted with halo, lower alkyl, cyano, nitro or alkoxy; (m) has a value of from 1 to 10; (b) has a value of from at least one up to 10 and (n−b) has a value of from 0 to 9.

2. A composition containing a mixture of compounds of claim 1.

3. The composition of claim 2 which also contains an oligomer of a compound at least one of said compounds in said mixture.

4. The compound of claim 1 wherein R' is hydrogen (m) is one.

5. The compound of claim 4 wherein B is butylene.

6. The compound of claim 4 wherein B is —CH$_2$—C$_6$H$_{10}$—CH$_2$—.

* * * * *